(12) United States Patent
Suetoshi et al.

(10) Patent No.: US 8,425,420 B2
(45) Date of Patent: Apr. 23, 2013

(54) BONE STRENGTH DIAGNOSING DEVICE AND BONE STRENGTH DIAGNOSING METHOD

(75) Inventors: Ryoichi Suetoshi, Nishinomiya (JP);
Shinji Ogawa, Nishinomiya (JP);
Atsushi Uodome, Nishinomiya (JP);
Takayoshi Nakano, Suita (JP); Yukichi Umakoshi, Suita (JP)

(73) Assignee: Furuno Electric Co., Ltd., Hyogo (JP)

( * ) Notice: Subject to any disclaimer, the term of this patent is extended or adjusted under 35 U.S.C. 154(b) by 550 days.

(21) Appl. No.: 12/601,868

(22) PCT Filed: Mar. 7, 2008

(86) PCT No.: PCT/JP2008/054129
§ 371 (c)(1),
(2), (4) Date: Feb. 16, 2010

(87) PCT Pub. No.: WO2008/146513
PCT Pub. Date: Dec. 4, 2008

(65) Prior Publication Data
US 2010/0185086 A1    Jul. 22, 2010

(30) Foreign Application Priority Data
May 29, 2007    (JP) .................................. 2007-141555

(51) Int. Cl.
*A61B 8/00*            (2006.01)
(52) U.S. Cl.
USPC ....................................................... 600/438
(58) Field of Classification Search ................... 600/438
See application file for complete search history.

(56) References Cited

U.S. PATENT DOCUMENTS

| | | | |
|---|---|---|---|
| 6,221,019 B1 * | 4/2001 | Kantorovich | 600/449 |
| 7,112,173 B1 | 9/2006 | Kantorovich et al. | |
| 2005/0004457 A1 | 1/2005 | Moilanen et al. | |
| 2005/0010106 A1 * | 1/2005 | Lang et al. | 600/425 |

FOREIGN PATENT DOCUMENTS

| | | |
|---|---|---|
| CN | 1297527 A | 5/2001 |
| CN | 1596084 A | 3/2005 |
| DE | 698 18 522 T2 | 7/2004 |
| JP | 7-100136 A | 4/1995 |
| JP | 2003-517328 A | 5/2003 |
| JP | 2005-510283 A | 4/2005 |

OTHER PUBLICATIONS

Mizukawa et al., "Elastic Anisotropy and Crystallites Orientation in Bovine Cortical Bones", Proceedings of 2006 IEEE Ultrasonics Symposium, 2006. 10, pp. 2120-2123.

* cited by examiner

*Primary Examiner* — Jonathan Cwern
(74) *Attorney, Agent, or Firm* — Birch, Stewart, Kolasch & Birch, LLP (57) ABSTRACT

The purpose of the current invention is to provide a bone strength diagnosing device and a bone strength diagnosing method capable of accurately diagnosing a bone strength of a bone. A longitudinal ultrasonic transducer and a transverse ultrasonic transducer radiate ultrasonic waves onto a bone front surface of a tibia from a predetermined angle to generate surface waves that propagate in the bone front surface in a longitudinal direction of the tibia and in a direction perpendicular to the longitudinal direction, respectively, and receive leaky waves leaking to the side of the soft tissues from the front surface waves. A speed-of-sound calculating module calculates speeds of sound of the surface waves in the transverse direction and the longitudinal direction based on a difference between course lengths of the ultrasonic waves and a difference between propagation times.

3 Claims, 9 Drawing Sheets

BONE STRENGTH DIAGNOSING DEVICE AND BONE STRENGTH DIAGNOSING METHOD

TECHNICAL FIELD

The present invention relates to a bone strength diagnosing device and a bone strength diagnosing method for diagnosing a bone strength using an ultrasonic wave.

BACKGROUND

Conventionally, although there are diagnosing devices for precisely measuring a bone density as devices for diagnosing a bone strength using X-rays, they have a problem that the devices are large-scaled and one may be irradiated.

For this reason, devices utilizing an ultrasonic wave are used as noninvasive bone strength diagnosing devices which do not cause such a problem (for example, refer to JP2005-510283(A)). With such a diagnosing device, an ultrasonic wave is radiated from a wave-transmission device of the ultrasonic wave in a direction inclined by a predetermined angle with respect to a front surface of the bone to generate a surface wave on the front surface of the bone. Then, for example, a leaky wave leaking from the surface wave is received by a wave-reception device of the ultrasonic wave which is movable relative to the wave-transmission device of the ultrasonic wave, and after that, a speed of sound of the surface wave is measured based on a propagation time and a propagation distance from the radiation of the ultrasonic wave to the reception of the leaky wave. Such a device measures a long bone, such as a radius, a tibia, and a phalange, and therefore, it measures a speed of sound of the surface wave transmitted in the long bone along the longitudinal direction. Generally, the bone strength is diagnosed to be higher as the speed of sound of the measured surface wave becomes faster.

SUMMARY

Problem(s) to be Solved by the Invention

However, the present inventors have found that, because an actual bone density may be low even when the speed of sound of the measured surface wave is fast, and conversely, the actual bone density may be high even when the speed of sound of the measured surface wave is slow, the speed of sound of the surface wave of the long bone in the longitudinal direction has a poor correlation with the bone density. Therefore, it is difficult to accurately evaluate the bone strength based on the speed of sound of the surface wave of the long bone in the longitudinal direction.

Consequently, the present invention aims at providing a bone strength diagnosing device and a bone strength diagnosing method capable of more accurately diagnosing the bone strength of a bone.

In addition, the present invention aims at providing a bone strength diagnosing device and a bone strength diagnosing method capable of measuring ex vivo "a cortical bone thickness" using an ultrasonic wave diagnosing device, an X-ray diagnosing device, computerized tomographic device or the like, and "a speed of sound in each axial direction" using an ultrasonic wave, to be able to observe a bone quantity from the cortical bone thickness, a bone density from a speed of sound in the circumferential or radial direction, and a bone orientation using a speed of sound in the longitudinal direction, as well as capable of diagnoses the bone strength based on viewpoints which are greater in number than those of the related art.

Means for Solving Problem(s) and Advantageous Effect(s) of the Invention

A bone strength diagnosing device according to the present application is a bone strength diagnosing device for diagnosing a bone strength using an ultrasonic wave, includes a speed-of-sound measuring device for radiating an ultrasonic wave onto a front surface of a bone, and measuring the speed of sound of the ultrasonic wave propagating on the front surface of the bone along a first direction that intersects with a longitudinal direction of the bone, a first index calculating device for calculating a first index related to a bone density using the speed of sound in the first direction measured by the speed-of-sound measuring device, and a bone diagnosing device for diagnosing the bone strength based on the first index calculated by the first index calculating device.

Generally, it can be considered that the speed of sound of an ultrasonic wave (surface wave) that propagates on a front surface of a bone is influenced by characteristics of the bone, such as a bone density, bone orientation, etc. The bone has a structure in which hydroxyapatite crystals and collagen fibers are arranged regularly. A long bone has an orientation of hydroxyapatite (HAp) crystals called a single-axis orientation in which the c-axis of the HAp crystals is arranged along the longitudinal direction. The running direction (orientation) of the fibrous collagen is almost the same as the c-axis direction of this HAp crystal. It can be considered that the speed of sound of the surface wave in the longitudinal direction is greatly influenced by both the orientation (the orientation of the HAp crystals and the orientation of the collagen fibers) of the bone in the longitudinal direction and the bone density, and therefore, the bone density cannot be grasped accurately from the speed of sound in the longitudinal direction. On the other hand, it can be considered that the speed of sound of the surface wave in the first direction that intersects with the longitudinal direction is less influenced by the bone orientation, and is greatly influenced by the correlation with the bone density. Therefore, the first index calculating device can calculate the first index related to the bone density based on the speed of sound in the first direction. The bone diagnosing device can diagnose the bone strength accurately by diagnosing the bone strength based on this first index, compared with the case where the bone strength is diagnosed based on the speed of sound in the longitudinal direction.

In the bone strength diagnosing device according to the present application, the speed-of-sound measuring device further may measure a speed of sound of an ultrasonic wave propagating along a second direction parallel to the longitudinal direction of the bone. The bone strength diagnosing device may further include a second index calculating device for calculating a second index related to an orientation of the bone using the speed of sound in the second direction and the speed of sound in the first direction measured by the speed-of-sound measuring device. The bone diagnosing device may diagnose the bone strength based on both the first index related to the bone density and the second index related to the bone orientation.

The speed of sound in the second direction is greatly influenced by the bone orientation and the bone density, the speed of sound in the first direction is less influenced by the bone orientation and is greatly influenced by the bone density. Therefore, the second index calculating device can calculate the second index related to the bone orientation based on the speed of sound in the second direction and the speed of sound in the first direction. The bone diagnosing device can diagnose the bone strength more accurately by diagnosing the bone strength using both the first index related to the bone density and the second index related to the bone orientation, compared with the case where it diagnoses only using the first index.

In the bone strength diagnosing device according to the present application, the first direction may be a direction perpendicular to the longitudinal direction of the bone.

The speed of sound of the surface wave in the direction perpendicular to the longitudinal direction is less influenced by the bone orientation. Therefore, the bone strength can be accurately diagnosed by using the speed of sound of the surface wave in the direction perpendicular to the longitudinal direction.

In the bone strength diagnosing device according to the present application, the speed-of-sound measuring device may further measure a cortical bone thickness of the bone. The bone strength diagnosing device may further include a third index calculating device for calculating a third index related to the bone strength using the cortical bone thickness measured by the speed-of-sound measuring device. The bone diagnosing device may diagnose the bone strength using both the first index related to the bone density and the third index related to the bone strength, or at least one of the first index related to the bone density, the second index related to the bone orientation, and the third index related to the bone strength.

The present osteoporosis diagnosis uses, as a standard, the bone mineral density (hereinafter, referred to as a "$BMD_{DXA}$") measurement according to the Dual X-ray Absorptiometry (hereinafter, referred to as "DXA"), and the $BMD_{DXA}$ which is a standard index of the bone strength is greatly influenced by the cortical bone thickness (bone quantity) rather than the cortical bone density. The third index calculating device calculates the third index related to the bone strength based on the cortical bone thickness of the bone measured with the ultrasonic wave. The bone diagnosing device can diagnose the bone strength more accurately by diagnosing the bone strength using the third index related to the bone strength in addition to the first index related to the bone density and the second index related to the bone orientation, compared with the case where it diagnoses only using the first index or it diagnoses only using the first index and the second index.

In the bone strength diagnosing device according to the present application, the speed-of-sound measuring device may radiate the ultrasonic wave onto the front surface of the bone substantially perpendicularly, receive a first reflective wave from the front surface of the bone and a second reflective wave from a back surface of the bone, and calculate a thickness of the bone based on the time difference between the wave receptions of the first reflective wave and the second reflective wave.

When the ultrasonic wave is transmitted to the bone substantially perpendicularly, the first reflective wave reflected on the front surface of the bone and the second reflective wave which propagates the inside of the bone and is reflected on the bone back surface occur. The speed-of-sound measuring device receives the first reflective wave and the second reflective wave after transmitting the ultrasonic wave to the bone. The second reflective wave returns with a delay by which it goes back and forth between the front surface and the back surfaces of the bone, with respect to the first reflective wave. That is, the time lag of the two reflective waves corresponds to a time for the ultrasonic wave to go back and forth between the bone front surface and the bone back surface. Therefore, the speed-of-sound measuring device can calculate the thickness of the bone based on the difference between the wave-reception times of the first reflective wave and the second reflective wave.

In the bone strength diagnosing device according to the present application, the thickness of the bone may be calculated using the time difference between the wave receptions and an assumed value of the speed of sound of the ultrasonic wave propagating in the bone.

The thickness of the bone can be calculated based on the speed of sound of the ultrasonic wave propagating in a thickness direction inside the bone, and the time difference between the wave receptions of the first reflective wave and the second reflective wave. Although any of the speeds of sound in the bone and the thickness of the bone has an individual specificity, a variation of the speed of sound in the bone due to the individual specificity is less compared with a variation of thickness of the bone due to the individual specificity. Therefore, by calculating the thickness of the bone while assuming the speed of sound in the bone to be a constant value, the thickness of the bone can be easily calculated.

The bone strength diagnosing device according to the present application may be what measures the cortical bone thickness of the bone by the cortical bone measuring device. It may further include a third index calculating device for calculating a third index related to the bone strength using the cortical bone thickness of the bone measured by the cortical bone measuring device. The bone diagnosing device may diagnose the bone strength based on both the first index related to the bone density and the third index related to the bone strength.

The bone strength diagnosing device according to the present application may be what measures the cortical bone thickness of the bone by the cortical bone measuring device. It may further include a third index calculating device for calculating a third index related to the bone strength using the cortical bone thickness measured by the cortical bone measuring device. The bone diagnosing device may diagnose the bone strength using at least one of the first index related to the bone density, the second index related to the bone orientation, and the third index related to the bone strength.

The cortical bone measuring device according to the present application may be a measuring device using an ultrasonic wave, an X-ray diagnosing device, or a computerized tomographic device.

The present osteoporosis diagnosis uses, as a standard, the bone mineral density (hereinafter, referred to as a "$BMD_{DXA}$") measurement according to the Dual X-ray Absorptiometry (hereinafter, referred to as "DXA"), and the $BMD_{DXA}$ which is a standard index of the bone strength is greatly influenced by the cortical bone thickness (bone quantity) rather than the cortical bone density. The third index calculating device calculates the third index related to the bone strength based on the cortical bone thickness of the bone measured by the cortical bone measuring device, such as a measuring device using an ultrasonic wave, an X-ray diagnosing device, or a computerized tomographic device. The bone diagnosing device can diagnose the bone strength more accurately by diagnosing the bone strength using the third index related to the bone strength in addition to the first index related to the bone density and the second index related to the bone orientation, compared with the case where it diagnoses only using the first index or it diagnoses only using the first index and the second index.

A bone strength diagnosing method according to the present application is a method of diagnosing a bone strength using an ultrasonic wave, including a speed-of-sound measuring step for radiating an ultrasonic wave onto a front surface of a bone, and measuring a speed of sound of the ultrasonic wave propagating on the front surface of the bone along a first direction that intersects with a longitudinal direction of the bone and a speed of sound of the ultrasonic wave propagating on the front surface of the bone along a second direction parallel to the longitudinal direction, a first index calculating step for calculating a first index related to a bone density using the speed of sound in the first direction measured by the speed-of-sound measuring step, a second index calculating step for calculating a second index related to an orientation of the bone using the speed of sound in the second direction and the speed of sound in the first direction measured by the speed-of-sound measuring step, and a bone diagnosing step for diagnosing the bone strength based on both the first index related to the bone density and the second index related to the bone orientation.

Because the speed of sound of the surface wave in the first direction is less influenced by the orientation and is greatly influenced by the bone density, it has high correlation with the bone density. On the other hand, the speed of sound of the surface wave in the second direction is greatly influenced by both the bone orientation and the bone density. Therefore, the first index related to the bone density can be calculated based on the speed of sound in the first direction by the first index calculating step. The second index related to the bone orientation can be calculated based on the speed of sound in the second direction and the speed of sound in the first direction by the second index calculating step. The bone strength can be more accurately diagnosed by diagnosing the bone strength using both the first index related to the bone density and the second index related to the bone orientation by the bone diagnosing step, compared with the case where only one of the indexes is used.

In the bone strength diagnosing method according to the present application, the speed-of-sound measuring steps may further measure a cortical bone thickness of the bone. The method may further include a third index calculating step for calculating a third index related to the bone strength using the cortical bone thickness measured by the speed-of-sound measuring step. The bone diagnosing step may diagnose the bone strength based on both the first index related to the bone density and the third index related to the bone strength, or at least one of the first index related to the bone density, the second index related to the bone orientation, and the third index related to the bone strength.

The bone strength diagnosing method according to the present application may be what measures the cortical bone thickness of the bone by the cortical bone measuring step. The method may further include a third index calculating step for calculating a third index related to the bone strength using the cortical bone thickness measured by the cortical bone measuring step. The bone diagnosing step may diagnose the bone strength based on both the first index related to the bone density and the third index related to the bone strength, or at least one of the first index related to the bone density, the second index related to the bone orientation, and the third index related to the bone strength.

The cortical bone measuring step according to the present application may be a measuring step using an ultrasonic wave, an X-ray diagnosing step, or a computerized tomographic step.

The present osteoporosis diagnosis uses, as a standard, the bone mineral density (hereinafter, referred to as a "BMD-$_{DXA}$") measurement according to the Dual X-ray Absorptiometry (hereinafter, referred to as "DXA"), and the BMD$_{DXA}$ which is a standard index of the bone strength is greatly influenced by the cortical bone thickness (bone quantity) rather than the cortical bone density. The third index calculating device calculates the third index related to the bone strength based on the cortical bone thickness of the bone measured by the cortical bone measuring device, such as a measuring device using an ultrasonic wave, an X-ray diagnosing device, or a computerized tomographic device. The bone diagnosing device can diagnose the bone strength more accurately by diagnosing the bone strength using the third index related to the bone strength in addition to the first index related to the bone density and the second index related to the bone orientation, compared with the case where it diagnoses only using the first index or it diagnoses only using the first index and the second index.

DESCRIPTION OF REFERENCE NUMERALS

1 Bone Strength Diagnosing Device
2 Transverse Ultrasonic Transducer
3 Longitudinal Ultrasonic Transducer
4 Device Main Body
5a and 5b Wave-transmission Module
6a, 6b, 7a, and 7b Wave-reception Module
8a and 8b Contact Face
20 Ultrasonic Control Module
21 Speed-of-sound Calculating Module
22 First Index Calculating Module
23 Second Index Calculating Module
24 Third Index Calculating Module
25 Bone Diagnosing Module
26 Display Module
30 Bone
31 Bone Front Surface
40 Soft Tissues
41 Skin Front Surface 100 Cortical Bone Measuring Device (X-ray Diagnosing Device, Computerized Tomographic Device)

DETAILED DESCRIPTION

Hereafter, an embodiment of the present invention will be described.

A bone strength diagnosing device 1 of this embodiment is a device for radiating an ultrasonic wave to a bone as a measurement part to generate a surface wave on a front surface of the bone, receives a leaky wave which leaks from the surface wave to measure a speed of sound of the surface wave, and then diagnoses a bone strength based on the obtained speed of sound.

Figure 2:
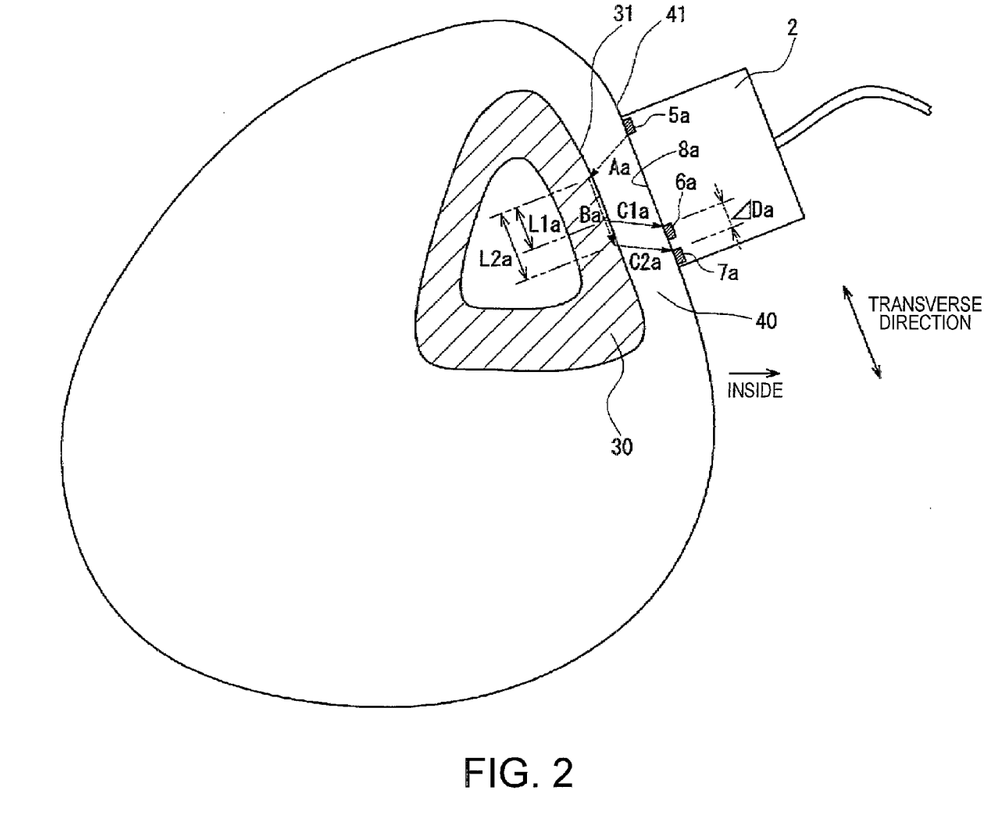
FIG. 2 is a cross-sectional view at the time of using a transverse ultrasonic transducer.

The bone strength diagnosing device 1 measures a medial surface of a tibia 31 as the measurement part. The tibia is a type of long bone, and as shown in FIG. 2, a cortical bone 30 of the tibia has a cross-sectional shape in a direction perpendicular to the longitudinal direction thereof, of substantially a triangle shape. The medial surface of the tibia 31, which is the measurement part, refers to a surface located inside a body (right side in FIG. 2) among three surfaces constituting the shape of the substantially triangle cross-section. The medial surface of the tibia 31 is flat over a predetermined length. A thickness of soft tissues 40, such as muscles covering this medial surface of the tibia 31, is relatively thin. Therefore, the medial surface of the tibia 31 is substantially parallel with a skin surface 41. For this reason, the surface wave described later can be generated, and a propagation distance of the surface wave can be secured.

Note that, in the following description of the bone strength diagnosing device 1, a longitudinal direction is defined as the longitudinal direction of the tibia and, and a transverse direction is defined as the direction perpendicular the longitudinal direction of the tibia and a direction of the medial surface of the tibia 31 shown in FIG. 2. Further, the medial surface of the tibia 31 and the cortical bone 30 of the tibia are simply indicated as the bone front surface 31 and the bone 30, respectively. A first direction and a second direction defined in the present invention correspond to the transverse direction and a longitudinal direction, respectively.

Figure 1:
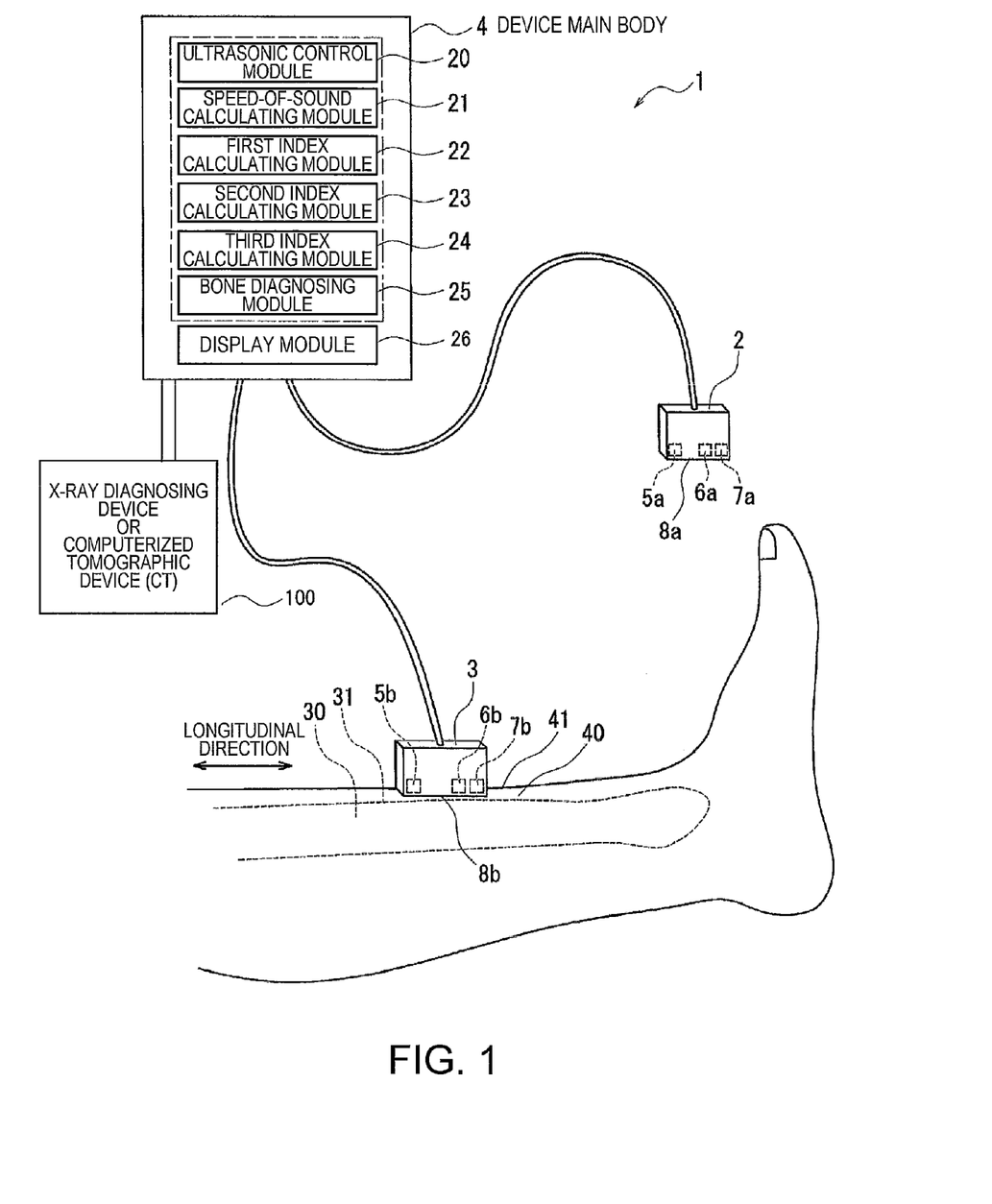
FIG. 1 is a view showing a bone strength diagnosing device according to an embodiment of the present invention.

As shown in FIG. 1, the bone strength diagnosing device 1 includes an ultrasonic transducer 2 for transverse direction, an ultrasonic transducer 3 for longitudinal direction, and a device main body 4. The transverse ultrasonic transducer 2 and the longitudinal ultrasonic transducer 3 are connected to the device main body 4 via cables, respectively.

Further, the bone strength diagnosing device 1 is provided with an interface (not illustrated) which is connectable with a cortical bone measuring device, such as a measuring device using the ultrasonic wave, an X-ray diagnosing device, a computerized tomographic device or the like, or what can share data measured by the cortical bone measuring device.

Alternatively, a wave-transceiver module for measuring a thickness of the cortical bone may be provided to at least one of the transverse ultrasonic transducer 2 and the longitudinal ultrasonic transducer 3, and the ultrasonic wave may be radiated substantially perpendicular to the bone, and based on a time lag of reflective waves on the front surface and the back surface, the thickness may be derived while assuming the speed of sound.

In this case, it is not necessary to be connected with the cortical bone measuring device, or it is not necessary to share the data.

The transverse ultrasonic transducer 2 radiates an ultrasonic wave to the bone front surface 31 to generate an ultrasonic wave (surface wave) propagating in the transverse direction along the bone front surface 31, and then receives an ultrasonic wave (leaky wave) leaking from the surface wave to the side of the soft tissues 40. The longitudinal ultrasonic transducer 3 radiates an ultrasonic wave to the bone front surface 31 to generate an ultrasonic wave (surface wave) propagating in the longitudinal direction along the bone front surface 31, and then receives an ultrasonic wave (leaky wave) leaking from the surface wave to the side of the soft tissues 40. For the transverse ultrasonic transducer 2 and the longitudinal ultrasonic transducer 3, an instrument called "ultrasonic transducer" for performing wave transmission and wave reception of the ultrasonic wave by a single instrument is used. Note that FIG. 2 is a view showing a state in which the transverse ultrasonic transducer 2 is used, and FIGS. 1 and 3 are views showing a state in which the longitudinal ultrasonic transducer 3 is used.

Figure 3:
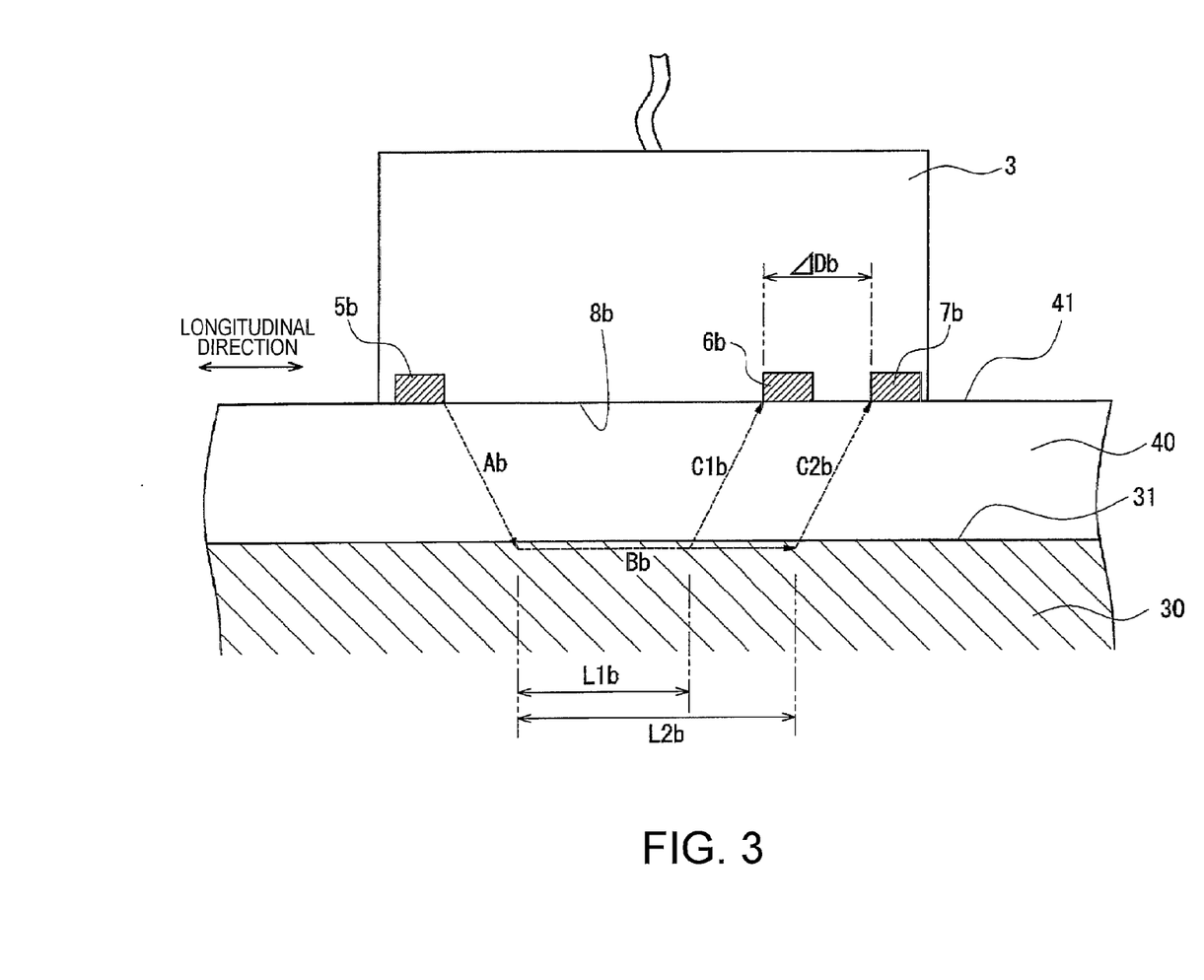
FIG. 3 is a cross-sectional view at the time of using a longitudinal ultrasonic transducer.

As shown in FIGS. 2 and 3, the transverse ultrasonic transducer 2 and the longitudinal ultrasonic transducer 3 are provided with contact faces 8a and 8b that comes in contact with the skin surface 41, respectively. An ultrasonic jelly is applied to the skin surface 41 when using the transverse ultrasonic transducer 2 and the longitudinal ultrasonic transducer 3.

As shown in FIG. 2, the transverse ultrasonic transducer 2 includes a wave-transmission module 5a for transmitting an ultrasonic wave, and two wave-reception modules 6a and 7a for receiving the ultrasonic wave. In a state in which the contact face 8a contacts a predetermined position on the skin surface 41, the wave-transmission module 5a, the wave-reception module 6a, and the wave-reception module 7a are spaced by predetermined intervals, and are arranged in this order in the transverse direction.

The wave-transmission module 5a radiates an ultrasonic pulse Aa at a predetermined frequency after receiving an electric pulse signal transmitted from the device main body 4. For the wave-transmission module 5a, what radiates an ultrasonic wave of a wide directivity is used. In the state in which the contact face 8a contacts the predetermined position on the skin surface 41, the wave-transmission module 5a is set so that the ultrasonic wave Aa radiated from the wave-transmission module 5a enters into the bone front surface 31 near at a critical angle. By using the wave-transmission module 5a with the wide directivity, even if the incident angle is not set strictly, the ultrasonic wave can enter into the bone front surface 31 at the critical angle. The critical angle can be derived from a speed of sound in the soft tissues 40 and a speed of sound of the surface wave described later. Therefore, by using the wave-transmission module 5a with a wide directivity, even if the speed of sound of the surface wave differs on examinees, the ultrasonic wave can enter into the bone front surface 31 at the critical angle.

When the ultrasonic pulse Aa is radiated from the wave-transmission module 5a and it enters into the bone front surface 31 at the critical angle, a surface wave Ba occurs on the bone front surface 31. The surface wave Ba radiates leaky waves in a predetermined direction on the side of the soft tissues 40, while propagating in the transverse direction along the bone front surface 31 (for example, the direction of C1a and C2a).

The two wave-reception modules 6a and 7a receive the leaky waves C1a and C2a radiated from the surface wave Ba which propagated for predetermined distances L1a and L2a, respectively. The wave-reception modules 6a and 7a receive the leaky waves C1a and C2a, respectively, and at the same time, they transmit arrival signals to the device main body 4, respectively.

As shown in FIG. 3, the longitudinal ultrasonic transducer 3 includes a wave-transmission module 5b for transmitting an ultrasonic wave, and two wave-reception modules 6b and 7b for receiving the ultrasonic wave similar to the transverse ultrasonic transducer 2. In a state in which the contact face 8b contacts the predetermined position on the skin surface 41, the wave-transmission module 5b, the wave-reception module 6b, and the wave-reception module 7b are spaced by predetermined intervals, and are arranged in this order in the longitudinal direction.

The wave-transmission module 5b radiates an ultrasonic pulse Ab at a predetermined frequency after receiving an electric pulse signal transmitted from the device main body 4. For the wave-transmission module 5a, what radiates an ultrasonic wave with a wide directivity is used. In the state in which the contact face 8b contacts the predetermined position on the skin surface 41, the wave-transmission module 5b is set so that the ultrasonic wave Ab radiated from the wave-transmission module 5b enters into the bone front surface 31 near at a critical angle.

When the ultrasonic pulse Ab is radiated from the wave-transmission module 5b and enters into the bone 30 at the critical angle, the surface wave Bb occurs on the bone front surface 31. The surface wave Bb radiates leaky waves in a predetermined direction on the side of the soft tissues 40, while propagating in the longitudinal direction along the bone front surface 31 (for example, the direction of C1b and C2b).

The two wave-reception modules 6b and 7b receive the leaky waves C1b and C2b radiated from the surface wave Bb, which propagated over predetermined distances L1b and L2b, respectively. The wave-reception modules 6b and 7b receive the leaky waves C1b and C2b, respectively, and at the same time, they transmit an arrival signal to the device main body 4, respectively.

As shown in FIG. 1, the device main body 4 includes an ultrasonic control module 20, a speed-of-sound calculating module 21, a first index calculating module 22, a second index calculating module 23, a bone diagnosing module 25, and a display module 26. Note that the ultrasonic control module 20, the speed-of-sound calculating module 21, the bone characteristic evaluating module 22, and the bone diagnosing module 25 are constituted with a ROM, RAM, CPU, etc. A speed-of-sound measuring device defined in the present invention includes the longitudinal ultrasonic transducer 3, the longitudinal ultrasonic transducer 3, the ultrasonic control module 20, and the speed-of-sound calculating module 21.

The ultrasonic control module 20 generates the electric pulse signals for radiating the ultrasonic pulses Aa and Ab at predetermined frequencies from the wave-transmission modules 5a and 5b of the transverse ultrasonic transducer 2 and the longitudinal ultrasonic transducer 3, respectively, and then transmits the electric signals to the transverse ultrasonic transducer 2 and the longitudinal ultrasonic transducer 3.

The speed-of-sound calculating module 21 calculates a speed of sound Va of the surface wave Ba transmitted over the bone front surface 31 in the transverse direction, based on a time lag or the like of arrival signals transmitted from the wave-reception modules 6a and 7a of the transverse ultrasonic transducer 2. In addition, the speed-of-sound calculating module 21 calculates a speed of sound Vb of the surface wave transmitted over the bone front surface 31 in the longitudinal direction based on a time lag or the like of arrival signals transmitted from the wave-reception modules 6b and 7b of the longitudinal ultrasonic transducer 3.

The case where the speed of sound Va of the surface wave Ba in the transverse direction is calculated will be described concretely. First, a time lag $\Delta Ta$ of the arrival signals transmitted from the wave-reception modules 6a and 7a is calculated. A difference between a course of the ultrasonic wave from the wave-transmission module 5a to the wave-reception module 6a and a course of the ultrasonic wave from the wave-transmission module 5a to the wave-reception module 7a is only a difference $\Delta La$ (L2a-L1a) of the propagation distances of the surface wave Ba in the transverse direction. That is, the surface wave Ba advances only a distance $\Delta La$ during the time $\Delta Ta$. As described above, because the bone front surface 31 and the skin surface 41 are substantially parallel to each other, the difference $\Delta La$ of the propagation distances of the surface wave Ba is substantially equal to the spaced distance $\Delta Da$ between the wave-reception module 6a and the wave-reception module 7a. Therefore, the speed of sound Va of the surface wave Ba in the transverse direction can be calculated by $Va=\Delta Da/\Delta Ta$.

When calculating the speed of sound Vb of the surface wave Bb in the longitudinal direction, assuming that the time lag of the arrival signals transmitted from the wave-reception modules 6b and 7b is $\Delta Tb$ and the spaced distance between the wave-reception module 6b and the wave-reception module 7b is $\Delta Db$, the speed of sound Vb of the surface wave Bb in the longitudinal direction can be calculated by $Vb=\Delta Db/\Delta Tb$.

The first index calculating module 22 treats the speed of sound Va of the surface wave in the transverse direction calculated by the speed-of-sound calculating module 21 as a first index related to a bone density. The second index calculating module 23 calculates a second index related to a bone orientation using the speeds of sound Vb and Va of the surface waves in the longitudinal direction and the transverse direction, respectively, calculated by the speed-of-sound calculating module 21. The bone diagnosing module 25 diagnoses a bone strength based on both the first index and the second index calculated by the first index calculating module 22 and the second index calculating module 23, respectively. Note that the first index calculating module 22, the second index calculating module 23, and the bone diagnosing module 25 will be described in detail later.

The display module 26 displays diagnostic results by the bone diagnosing module 25 along with the first index and the second index which are calculated by the bone characteristic evaluating module 22.

Here, a relation between the speed of sound of the surface wave, the bone density and the bone orientation, and the bone strength will be described.

It can be considered that the bone strength is mostly determined by the bone orientation and the bone density. The bone density is an evaluation index of the bone quantity and, thus, it shows a stuffed degree of the bone. A bone has a higher strength as its bone density becomes higher. Meanwhile, the bone orientation is one of the important indexes to evaluate a bone quality. Bone has a structure where hydroxyapatite (HAp) crystals and fibrous collagen are arranged regularly. The orientation of the HAp crystals represents an arrangement direction and an arrangement degree (a degree of regularly arrangement of the crystals) of the HAp crystals. The fibrous collagen also runs in almost the same direction as the arrangement direction of the HAp crystals. A long bone including the tibia has a characteristic called a single-axis orientation in which the c-axis of the HAp crystals is arranged along the longitudinal direction. Generally, if the arrangement degree of the HAp crystals is high in a certain arrangement direction, it can be judged that the bone strength is high in the arrangement direction. However, for example, if the bone density decreases due to osteoporosis, the orientation may become higher in the direction to which a load acts. This is considered for an action with which the lowered bone strength is compensated to work. Thus, when only the orientation in a specific direction becomes extremely high, the orientations in other directions may become lower and the bone strength may become weaker in the directions.

Further, it can be considered that the speed of sound of the surface wave of the bone is influenced by both the bone density and the bone orientation (the orientation of the HAp crystals and the orientation of collagen). It can be considered that, in the case of the same orientation, the speed of sound of the surface wave becomes faster as the bone density becomes higher, and in the case of the same bone density, the speed of sound of the surface wave becomes faster as the orientation becomes higher.

Figure 4:
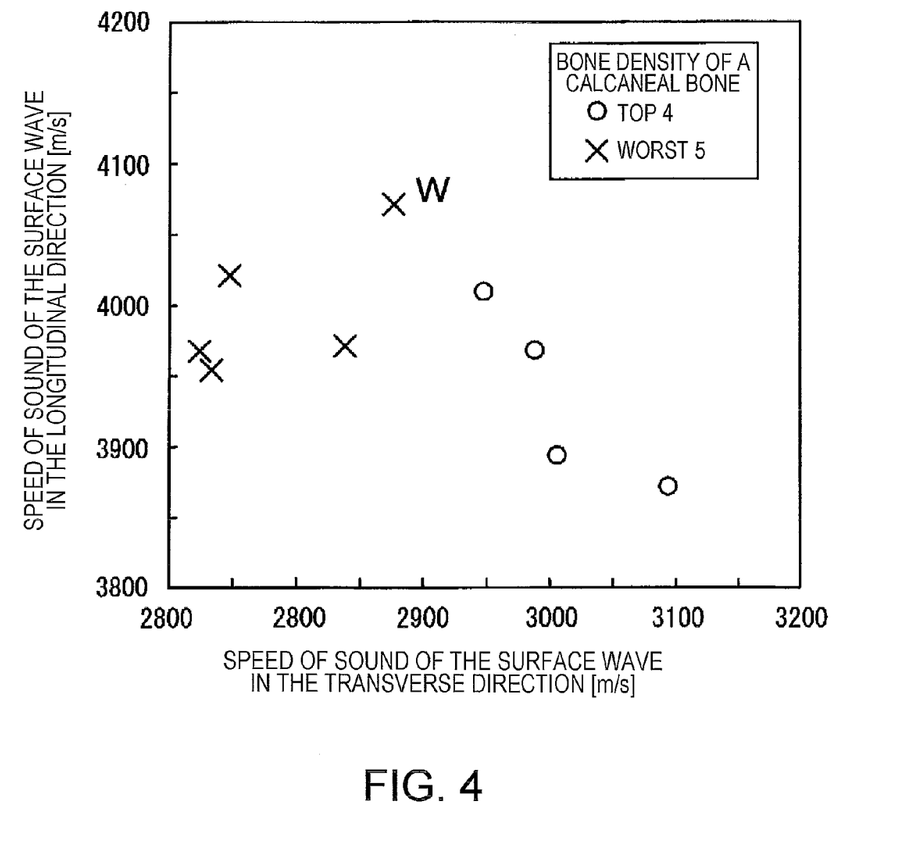
FIG. 4 is a graph showing a relation between speeds of sound of the surface waves in the longitudinal direction and the transverse direction of a tibia, and a bone density of a calcaneal bone.

FIG. 4 shows a graph showing a relevance of the speeds of sound of the surface waves of the tibia in the transverse direction and the longitudinal direction, and the bone density. In FIG. 4, the vertical axis is set to the speed of sound of the surface wave in the longitudinal direction, and the horizontal axis is set to the speed of sound of the surface wave in the transverse direction. First, the speeds of sound of the surface waves of the tibia in the transverse direction and the longitudinal direction are measured for two or more examinees. Further, for calcaneal bones of the same examinees, the bone densities are measured using an ultrasonic bone density measuring device (model CM-200 available from FURUNO ELECTRIC CO., LTD.). In FIG. 4, for the top four examinees in the bone density, the measurement results of the speeds of sound of the surface waves in the transverse direction and the longitudinal direction are indicated by symbols "O," and for the worst five examinees in the bone density, the measurement results of the speeds of sound of the surface waves in the transverse direction and the longitudinal direction are indicated by symbols "X." Note that the ultrasonic bone density measuring device used for the measurements of the bone densities of the calcaneal bones calculates the bone densities by pinching each calcaneal bone with an ultrasonic wave transmitter and an ultrasonic wave receiver, and measuring the speed of sound of an ultrasonic wave which passes through the inside of the calcaneal bone. Normally, if the bone density in a certain part is high, it can be presumed that the bone densities of other parts also become high. Therefore, when the bone density of the calcaneal bone is high, it is considered that the bone density of the tibia is also high.

As shown in FIG. 4, the speeds of sound of the surface waves in the transverse direction of the four examinees with high bone densities are relatively faster. On the other hand, the speeds of sound of the surface waves in the transverse direction of the five examinees with low bone densities are relatively slower. Therefore, the speed of sound of the surface wave in the transverse direction has correlation with the bone density, and when the speed of sound of the surface wave in the transverse direction is faster, it can be judged that the bone density is high. It can be considered that it originates in that the surface wave in the transverse direction propagates crossing the arrangement direction due to the single-axis orientation of the tibia described above, and therefore, the speed of sound of the surface wave in the transverse direction is seldom influenced by the orientation but greatly influenced by the bone density.

On the other hand, as shown in FIG. 4, for the four examinees with high bone densities, some have relatively faster speeds of sound of the surface waves in the longitudinal direction, and some have relatively slow speeds of sound. Therefore, even if the speed of sound of the surface wave in the longitudinal direction is fast (or slow), and it cannot be said that the bone density is high. It can be considered that it originates in that the surface wave in the longitudinal direction propagates along the arrangement direction due to the single-axis orientation of the tibia described above, and therefore, the speed of sound of the surface wave in the longitudinal direction is greatly influenced by both the orientation and the bone density.

From the above, the first index calculating module uses the speed of sound Va of the surface wave in the transverse direction per se as an index (first index) by which the bone density is evaluated.

Further, it can be considered that the speed of sound of the surface wave in the longitudinal direction is influenced by both the bone density and the orientation, and, on the other hand, the speed of sound of the surface wave in the transverse direction is less influenced by the orientation and is greatly influenced by the bone density. Therefore, it is considered that a value obtained by dividing the speed of sound of the surface wave in the longitudinal direction by the speed of sound of the surface wave in the transverse direction is cancelled out for the influence of the bone density, and has correlation with the orientation. Therefore, it can be judged that, for example, among the five examinees with small bone densities shown in FIG. 4, because the examinee with the fastest speed of sound W of the surface wave in the longitudinal direction has a relatively high value obtained by dividing the speed of sound of the surface wave in the longitudinal direction by the speed of sound of the surface wave in the transverse direction, the orientation is high.

From the above, the second index calculating module 23 calculates the value Vb/Va obtained by dividing the speed of sound Vb of the surface wave in the longitudinal direction by the speed of sound Va of the surface wave in the transverse direction, and then treats this value Vb/Va as the second index by which the orientation is evaluated.

Further, as described above, the bone strength is mostly determined by the bone density and the bone orientation, and the bone density and the bone orientation are mutually independent indexes of the bone strength. Therefore, the bone diagnosing module 25 diagnoses the bone strength based on the first index and the second index. If the first index is greater than a predetermined value, it can be diagnosed that the bone strength is sufficient from a viewpoint of the bone density. The second index is used by being checked with the first index. For example, when the first index is less than the predetermined value and the second index is a greater value than a predetermined range, the bone density is low but the orientation is high. In this case it can be considered that, because the bone density decreased by osteoporosis, the orientation in the longitudinal direction became high by a load, for example. In this case, it is diagnosed that the bone strength is low particularly in directions of other than the longitudinal direction. By diagnosing the bone strength based on both the bone density and the bone orientation, the bone strength can be diagnosed more accurately, compared with the case where it is diagnosed based on one of the indexes. Particularly, when the bone density and the bone orientation change according to osteoporosis or a child's bone growth, the bony condition can be grasped and diagnosed more accurately by using both the indexes, compared with the case where one of the indexes is used FIGS. 5 to 9 show data actually measured using bone test samples.

As the bone test samples, human femur diaphysial cortical bone parts of seventeen men and women aged from 70 to 94 are used. After measuring a DXA and a Peripheral Quantitative Computed Tomography (pQCT) applicable to the cortical bone measuring device 100, a bone sample (cortical bone) is cut out from a position of approximately 3 cm below the trochanter minor, and a cuboid block having one side of 1 cm or less is produced. The bone block is sandwiched by two probes, and then, the speeds of sound in the length-wise direction (longitudinal) and the circumferential direction (transverse) are measured by an ultrasonic penetration method (center frequency is 3 MHz). Further, the bone density is measured by the Archimedes method. The bone orientation in the longitudinal direction is measured, by a microscopic region X-ray diffraction method, a c-axis orientation of the living body apatite (BAp) crystals in each directions from (002)/(310) intensity ratio.

By analyzing the correlation between the respective parameters from the measured values described above, the correlation between the speed of sound according to the ultrasonic wave and a BMD or the crystal orientation by X-ray is examined.

Figure 5:
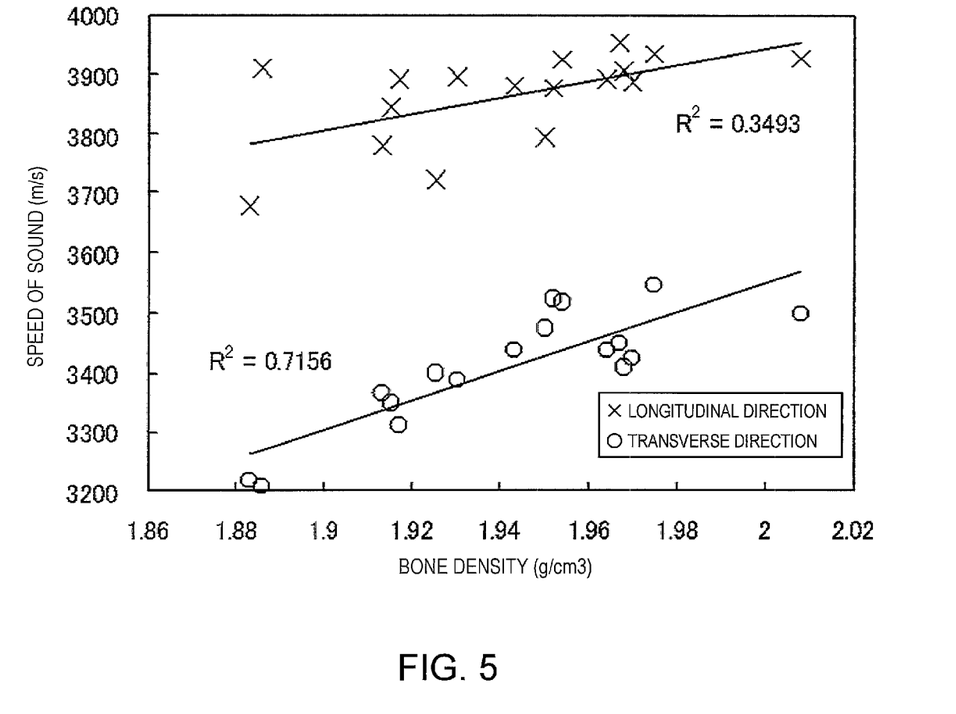
FIG. 5 is a graph showing a relation between a bone density of a human femur diaphysial cortical bone part and speeds of sound in the longitudinal and transverse directions.

FIG. 5 shows a relation between the bone density, and the speeds of sound in the longitudinal and transverse directions. First, it can be seen that the longitudinal speeds of sound are faster than the transverse speeds of sound, and their bone anisotropy are appeared in the speed of sound. It is shown that, as for a correlation coefficient with the bone density, it is greater in the transverse speed of sound ($R^2=0.72$) and, thus, the first index related to the bone density can be calculated from the speed of sound along the first direction which intersects with the longitudinal direction. It can be seen that the correlation between the longitudinal speed of sound and the bone density is $R^2=0.35$, which indicates a weak correlation.

Figure 6:
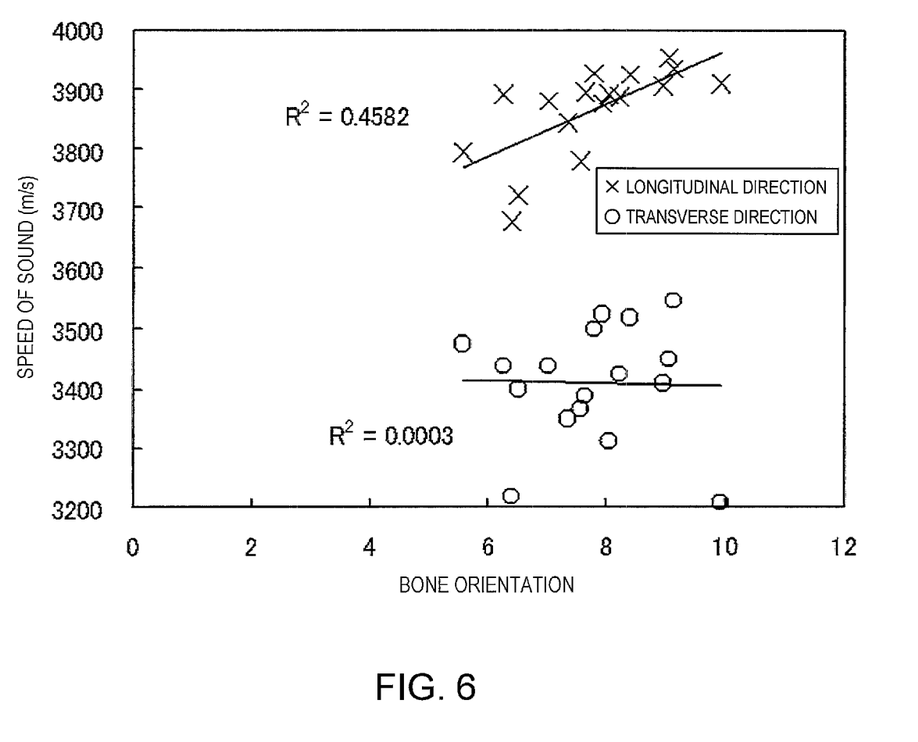
FIG. 6 is a graph showing a relation between an orientation of a bone of the human femur diaphysial cortical bone part and the speeds of sound in the longitudinal and transverse directions.

FIG. 6 shows a relation between the bone orientation and the speeds of sound in the longitudinal and transverse directions. The correlation between the bone orientation (apatite crystals) and the transverse speed of sound cannot be observed; however the correlation can be observed with the longitudinal speed of sound ($R^2=0.46$). It can be seen that it is not so large as the correlation coefficient of the bone density and the transverse speed of sound.

Figure 7:
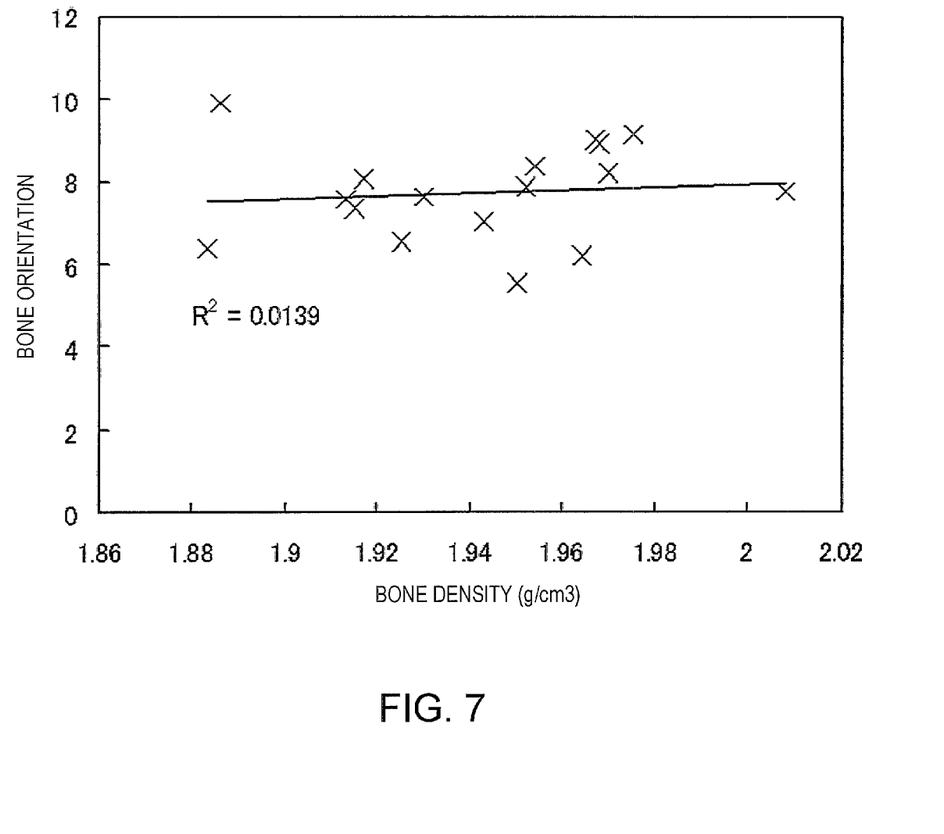
FIG. 7 is a graph showing a relation between the bone density of the human femur diaphysial cortical bone part and the bone orientation.

FIG. 7 shows a relation between the bone density and the bone orientation. It can be seen that there is no correlation between the bone density and the bone orientation and, thus, they are parameters independent from each other.

Figure 8:
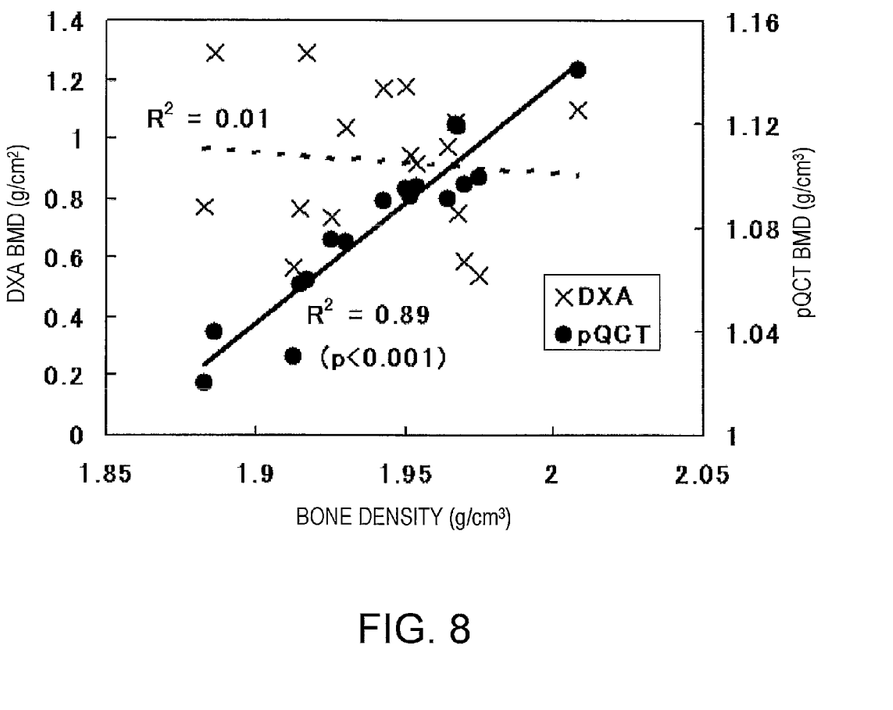
FIG. 8 is a graph showing a relation between the bone density of the human femur diaphysial cortical bone part and a BMD$_{DXA}$, as well as the bone density and a BMD$_{pQCT}$.
Figure 9:
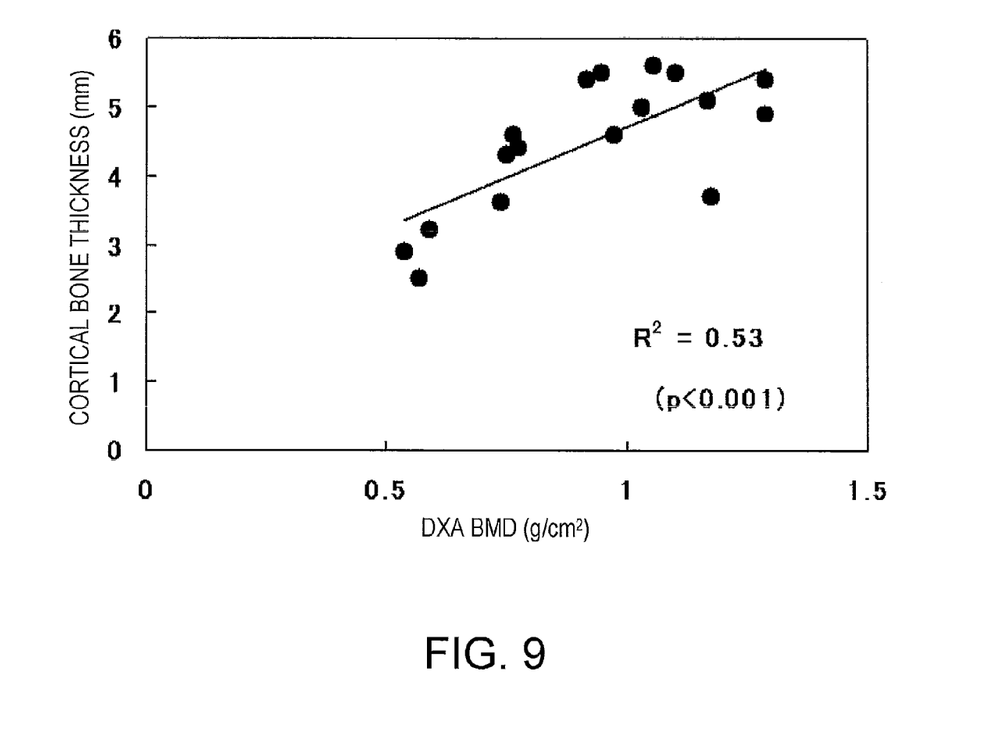
FIG. 9 is a graph showing a relation between a thickness of the bone of the human femur diaphysial cortical bone part and the BMD$_{DXA}$.

FIG. 8 shows a relation between the bone density, and a $BMD_{DXA}$ by a DXA method and a $BMD_{pQCT}$ by a pQCT method, and FIG. 9 shows a relation between the cortical bone thickness and the $BMD_{DXA}$ by the DXA method. In the pQCT, the $BMD_{pQCT}$ of the cut-out part is calculated and a thickness of the cortical bone in the vicinity thereof is also read. It can be seen that there is no correlation between the bone density and the $BMD_{DXA}$ by the DXA method, and there is correlation between the bone density and the $BMD_{pQCT}$ by the pQCT method. Thereby, it can be said that the $BMD_{DXA}$ which is a standard index of the bone strength is not what indicates a physical bone density. On the contrary, because the correlation was seen between the $BMD_{DXA}$ and the cortical bone thickness ($R^2=0.53$), it can be seen that the $BMD_{DXA}$ is dominant on not the bone density but the bone quantity.

FIGS. 5 to 8 and their multiple linear regression analyses show that both the parameters of the bone density and the bone orientation contribute to the longitudinal speed of sound. Here, by the multiple linear regression analyses, when the regression analyses are performed for the longitudinal speeds of sound with the two parameters of the bone density and the bone orientation, the correlation coefficient will improve to $R^2=0.85$. The standard regression coefficients of the bone orientation and the bone density will be 0.52 and 0.62, respectively. This indicates that the longitudinal speed of sound is reflected by a rate of contribution with similar bone orientation and bone density.

Therefore, the bone orientation can be calculated using both the indexes of the first direction speed of sound and the second direction speed of sound. From the above, it can be seen that the $BMD_{DXA}$, which is a standard index of the bone strength (measured by the DXA), is influenced greatly by the cortical bone thickness (bone quantity) rather than the cortical bone density. On the other hand, because it has been seen that the $BMD_{pQCT}$ and the cortical bone density which are measured by the pQCT has a strong correlation, it can be understood that the bone density is mostly determined by a quantity of mineral components. Further, for the bone anisotropy, it can be seen that the speeds of sound in the circumferential and radial directions are mostly influenced only by the bone density, and the speed of sound in the longitudinal direction is governed by both the bone density and the apatite crystal orientation. That is, by measuring "the cortical bone thickness" and "the speed of sound in each axial direction" ex vivo using the ultrasonic wave, it is possible to observe the bone quantity from the cortical bone thickness, the bone density from the circumferential or radial speed of sound, and the bone orientation using and the longitudinal speed of sound, and therefore, the bone strength can be diagnosed from more viewpoints than the related arts.

Next, a processing procedure at the time of diagnosing the bone strength using the bone strength diagnosing device 1 will be described. First, the contact face 8a of the transverse ultrasonic transducer 2 is made to contact with the skin surface 41 that covers the bone 30 of the measurement part onto which the ultrasonic jelly is applied. In this state, an operator turns on a switch provided to the device main body 4. Thereby, the electric signal is transmitted from the ultrasonic control module 20 of the device main body 4 to the transverse ultrasonic transducer 2. When the electric signal is received, the transverse ultrasonic transducer 2 radiates the ultrasonic pulse Aa in the predetermined inclined direction from the wave-transmission module 5a to the bone front surface 31. The radiated ultrasonic pulse Aa propagates in the soft tissues 40, and then enters into the bone 30 at the critical angle to generate the surface wave Ba on the bone front surface 31. This surface wave Ba propagates on the bone front surface 31 in the transverse direction, while being leaking to the side of the soft tissues 40. The leaky waves C1a and C2a leaking after the surface wave Ba propagated for the predetermined distances L1a and L2a are received by the wave-reception modules 6a and 7a, respectively. The wave-reception modules 6a and 7a receive the leaky waves C1a and C2a, respectively, and at the same time, they transmit the arrival signals to the device main body 4.

Next, the contact face 8b of the longitudinal ultrasonic transducer 3 is made to contact with the skin surface 41 that covers the bone 30 of the measurement part onto which the ultrasonic jelly is applied, and the switch of the device main body 4 is turned on. Thereby, the electric signal is transmitted from the ultrasonic control module 20 of the device main body 4 to the longitudinal ultrasonic transducer 3. When the electric signal is received, the longitudinal ultrasonic transducer 3 radiates the ultrasonic pulse Ab in the predetermined inclined direction from the wave-transmission module 5b to the bone front surface 31. The radiated ultrasonic pulse Ab propagates in the soft tissues 40, and then enters into the bone 30 at the critical angle to generate the surface wave Bb on the bone front surface 31. This surface wave Bb propagates on the bone front surface 31 in the longitudinal direction, while leaking to the side of the soft tissues 40. The leaky waves C1b and C2b leaking after the surface wave Bb propagated for the predetermined distances L1b and L2b are received by the wave-reception modules 6b and 7b, respectively. The wave-reception modules 6b and 7b receive the leaky waves C1b and C2b, respectively, and at the same time, they transmit the arrival signals to the device main body 4.

The speed-of-sound calculating module 21 of the device main body 4 calculates the speed of sound Va of the surface wave Ba in the transverse direction based on the time lag ΔTa of the two arrival signals transmitted from the transverse ultrasonic transducer 2, and the spaced distance ΔDa of the wave-reception modules 6a and 7a. Similarly, the speed of sound Vb of the surface wave Bb in the longitudinal direction is calculated based on the time lag ΔTb of the two arrival signals transmitted from the longitudinal ultrasonic transducer 3, and the spaced distance ΔDb of the wave-reception modules 6b and 7b.

Next, the first index using the speed of sound Va of the surface wave in the transverse direction is obtained by the first index calculating module 22. In addition, the value obtained by dividing the speed of sound Vb of the surface wave in the longitudinal direction by the speed of sound Va of the surface wave in the transverse direction is calculated by the second index calculating module 23 and, thus, the second index is obtained.

Next, the bone diagnosing module 25 diagnoses the bone strength based on the first index and the second index. Then, the display module 26 displays the diagnostic result of the bone diagnosing module 25 along with the first index and the second index.

Moreover, if connected with the cortical bone measuring device, such as a measuring device using an ultrasonic wave, an X-ray diagnosing device, a computerized tomographic device or the like, or when sharing the data measured by the cortical bone measuring device, a third index is also displayed on the display module 26 in addition to the two indexes described above.

Note that the bone strength diagnosing device 1 of this embodiment may be implemented with the following modifications.

1) The measurement part is not limited to the tibia, and may be any bones other than the tibia.

2) The transverse ultrasonic transducer 2 or the longitudinal ultrasonic transducer 3 may not have the configuration in which each has one wave-transmission module and two wave-reception modules. For example, it may have a configuration in which one has two wave-transmission modules and one wave-reception module. Alternatively, one may have one wave-transmission module and one wave-reception module, and either one of the wave-transmission module and the wave-reception module may have a configuration in which it is relatively movable to the other. Alternatively, one may have a configuration in which it has one wave-transmission module and three or more wave-reception modules.

3) The transverse ultrasonic transducer 2 and the longitudinal ultrasonic transducer 3 may not be separate modules. That is, a single ultrasonic transducer capable of being used for both the transverse direction and the longitudinal direction may be used.

4) The direction of the surface wave measured is not limited to the transverse direction (the direction perpendicular to the longitudinal direction) and the longitudinal direction (lengthwise direction), and it may be a direction other than the transverse direction which intersects with the longitudinal direction, and the longitudinal direction.

5) The speed-of-sound measuring device defined in the present invention is not limited to what is constituted with the transverse ultrasonic transducer 2, the longitudinal ultrasonic transducer 3, the ultrasonic control module 20, and the speed-of-sound calculating module 21. For example, the ultrasonic calculating device may have a configuration in which it includes a known device for removing noises, such as reflective waves.

6) The first index obtained by the first index calculating module 22 is not limited to the speed of sound Va of the surface wave in the transverse direction per se, and a value calculated based on the speed of sound Va may also be used. For example, the first index may be a value calculated based on the speed of sound Va of the surface wave in the transverse direction, the thickness of the soft tissues, etc.

7) The second index obtained by the second index calculating module 23 is not limited to the value obtained by dividing the speed of sound Vb of the surface wave in the longitudinal direction by the speed of sound Va of the surface wave in the transverse direction, and a value calculated by another method based on the speed of sound Va and the speed of sound Vb may also be used.

8) The bone strength diagnosing device 1 may not include the longitudinal ultrasonic transducer 3 and the second index calculating module 23. In this case, if the first index obtained from the speed of sound Va of the surface wave in the transverse direction is greater than the predetermined value, the bone diagnosing module 25 diagnoses that the bone density is high and the bone strength is high. Thereby, the bone strength can be diagnosed more accurately than the conventional devices for diagnosing a bone strength only based on the speed of sound of the surface wave in the longitudinal direction.

What is claimed is:

1. A bone strength diagnosing device for diagnosing a bone strength using an ultrasonic wave, comprising:
    a speed-of-sound measuring device for radiating an ultrasonic wave onto a front surface of a bone, and measuring
        a first speed of sound of the ultrasonic wave propagating on the front surface of the bone along a first direction that intersects with a longitudinal direction of the bone;
        a second speed of sound of an ultrasonic wave propagating along a second direction parallel to the longitudinal direction of the bone; and
        a cortical bone thickness of the bone;
    a first index calculating device for calculating a first index related to a bone density using the speed of sound in the first direction measured by the speed-of-sound measuring device;
    a second index calculating device for calculating a second index related to an orientation of the bone using the speed of sound in the second direction and the speed of sound in the first direction measured by the speed-of-sound measuring device;
    a third index calculating device for calculating a third index related to the bone strength using the cortical bone thickness measured by the speed-of-sound measuring device; and
    a bone diagnosing device for diagnosing the bone strength based on the first index related to the bone density, the second index related to the bone orientation, and the third index related to the bone strength.

2. The bone strength diagnosing device according to claim 1, wherein the first direction is a direction perpendicular to the longitudinal direction of the bone.

3. A method of diagnosing a bone strength using an ultrasonic wave, comprising:
    a speed-of-sound measuring step for radiating an ultrasonic wave onto a front surface of a bone, and measuring a speed of sound of the ultrasonic wave propagating on the front surface of the bone along a first direction that intersects with a longitudinal direction of the bone and measuring a speed of sound of the ultrasonic wave propagating on the front surface of the bone along a second direction parallel to the longitudinal direction and measuring a cortical bone thickness of the bone;

a first index calculating step for calculating a first index related to a bone density using the speed of sound in the first direction measured by the speed-of-sound measuring step;

a second index calculating step for calculating a second index related to an orientation of the bone using the speed of sound in the second direction and the speed of sound in the first direction measured by the speed-of-sound measuring step;

a third index calculating step for calculating a third index related to the bone strength using the cortical bone thickness measured by the speed-of-sound measuring step; and a bone diagnosing step for diagnosing the bone strength based on both the first index related to the bone density and the second index related to the bone orientation and the third index related to the bone strength.

* * * * *